(12) United States Patent
Noordhoek

(10) Patent No.: US 8,047,715 B2
(45) Date of Patent: Nov. 1, 2011

(54) MULTIPLE ROTATION C-ARM

(75) Inventor: Nicolaas Jan Noordhoek, Breda (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 45 days.

(21) Appl. No.: 12/513,368

(22) PCT Filed: Oct. 24, 2007

(86) PCT No.: PCT/IB2007/054317
§ 371 (c)(1),
(2), (4) Date: May 4, 2009

(87) PCT Pub. No.: WO2008/053402
PCT Pub. Date: May 8, 2008

(65) Prior Publication Data
US 2010/0067649 A1    Mar. 18, 2010

(30) Foreign Application Priority Data
Nov. 3, 2006   (EP) .................................. 06123446

(51) Int. Cl.
*H05G 1/06*   (2006.01)
(52) U.S. Cl. ........................................ 378/194; 378/197
(58) Field of Classification Search ................... 378/194, 378/193, 196, 197
See application file for complete search history.

(56) References Cited

U.S. PATENT DOCUMENTS

| | | |
|---|---|---|
| 4,065,978 A | 1/1978 | Meresz et al. |
| 4,163,526 A | 8/1979 | Williams |
| 5,166,952 A | 11/1992 | Omura et al. |
| 5,432,813 A | 7/1995 | Barham et al. |
| 5,666,379 A | 9/1997 | Ovard et al. |
| 6,113,264 A | 9/2000 | Watanabe |
| 6,542,270 B2 | 4/2003 | Perkins et al. |
| 6,582,120 B2 * | 6/2003 | Schomberg ................... 378/197 |
| 6,628,699 B2 | 9/2003 | Ramberg et al. |
| 6,733,177 B2 * | 5/2004 | Pillai et al. ..................... 378/198 |
| 7,187,757 B2 * | 3/2007 | Saint-Martin et al. ........ 378/130 |
| 7,224,769 B2 | 5/2007 | Turner |
| 7,912,182 B2 | 3/2011 | Van Der Ende |
| 2002/0168053 A1 | 11/2002 | Schomberg |
| 2003/0000198 A1 | 1/2003 | Hermey et al. |
| 2004/0196959 A1 | 10/2004 | Weston |
| 2005/0084060 A1 | 4/2005 | Seppi et al. |
| 2005/0117706 A1 * | 6/2005 | Powell ........................... 378/141 |
| 2007/0253540 A1 * | 11/2007 | Anderton et al. .............. 378/199 |
| 2009/0040333 A1 * | 2/2009 | Koyanagi .................... 348/223.1 |
| 2009/0180595 A1 * | 7/2009 | Spahn ............................ 378/197 |

FOREIGN PATENT DOCUMENTS

| | | |
|---|---|---|
| GB | 1582833 A | 1/1981 |
| WO | 2006095301 A1 | 9/2006 |

* cited by examiner

*Primary Examiner* — Hoon Song

(57) ABSTRACT

Current C-arm examination devices are not capable of performing 360 degrees rotations. The reason for this is that the cabling which connects the external cabinets to the detector, collimator and x-ray tube does not allow for such a rotation. According to an exemplary embodiment of the present invention, an examination apparatus is provided which has a connection device connecting the external cabinets to the C-arm which is adapted for enabling a rotation of the C-arm of more than 360 degrees. Such a connection device may comprise a storing device for winding up the cable.

19 Claims, 5 Drawing Sheets

MULTIPLE ROTATION C-ARM

The invention relates to the field of medical imaging. In particular, the invention relates to an examination apparatus for examination of an object of interest, to a method of examination of an object of interest, a computer-readable medium and a program element.

Currently, a range of new three-dimensional and four-dimensional applications are being developed based on C-arm scanners which may be limited in their speed, workflow, ease of use and image quality by the fact that a C-arm can only rotate from about −120 degrees to +180 degrees. This is caused by the electrical connections and cooling hoses that are connecting the rotating C-arm with the stationary stand/power cabinets. Both the electrical connections and cables and the cooling hoses are contained in a flexible hose which may only allow a limited rotational scan range (i.e. the angular range).

However, the new three-dimensional or four-dimensional applications under development may require multiple rotations. This may now only be achieved by making a partial rotation of less than 360° and then rotate slowly back in order to make another, following partial rotation.

It would be desirable to provide for an improved C-arm scanner.

According to an exemplary embodiment of the present invention, an examination apparatus for examination of an object of interest is provided, the examination apparatus comprising an x-ray C-arm module comprising a C-arm and an x-ray source, a stand for providing electrical power and cooling to the x-ray source and a connection device for providing a connection between the stand and the C-arm module for delivering the electrical power and the cooling to the x-ray source, wherein the connection device is adapted for enabling a rotation of the C-arm of more than 360 degrees.

Therefore, by providing a connection device connecting the stand and the C-arm module, which is capable for enabling a rotation of a C-arm of more than a full turn, may improve the image quality. Furthermore, by enabling more than a full turn of the C-arm, the rotational speed may further be increased.

According to another exemplary embodiment of the present invention, the connection device comprises a slip-ring for passing electrical signals and the electrical power from the stand to the C-arm module.

Such a slip-ring may allow the electrical signal and the high-voltage electrical power to pass from the stand to the C-arm module without disconnecting the electrical lines. Thus, a continuous rotation of the C-arm may be provided while maintaining the high-voltage supply.

According to another exemplary embodiment of the present invention, the slip-ring comprises a ring and sliding fingers, wherein the sliding fingers are adapted for sliding on the ring during rotation of the C-arm, thereby enabling the rotation and meanwhile maintaining electrical contact between corresponding electrical elements of the stand and electrical elements of the C-arm.

Furthermore, according to another exemplary embodiment of the present invention, the connection device comprises a rotating coupling for passing coolant from the stand to the C-arm module during rotation of the C-arm.

Therefore, cooling of the x-ray source may be provided continuously during multiple rotations of the C-arm.

According to another exemplary embodiment of the present invention, the connection device comprises a cable for delivering the electrical power to the x-ray source. The cable is arranged inside a hose, wherein the arrangement of cable and hose is adapted for storing at least four rotations of the C-arm.

Therefore, by providing an elongated cable/hose configuration connecting the stand to the C-arm, and by storing a plurality of rotations by the cable/hose arrangement, a following opposite rotation of the C-arm may be enabled without damaging the cable/hose.

According to another exemplary embodiment of the present invention, the examination apparatus further comprises a storing device for storing a part of the cable and adapted for gradually releasing the stored cable during the rotation of the C-arm.

The storing device is, according to another exemplary embodiment of the present invention, adapted as a square cable feeder that can only bend or roll in one direction.

Thus, the cable and cooling hose may be efficiently protected from mechanical damage when being rolled up into the storing device.

According to another exemplary embodiment of the present invention, the x-ray source is adapted for generating a polychromatic x-ray beam.

Furthermore, according to another exemplary embodiment of the present invention, the examination apparatus is configured as one of the group consisting of a material testing apparatus, a medical application apparatus and a micro CT system.

A field of application of the invention may be medical imaging, in particular cardiac CT.

According to another exemplary embodiment of the present invention, the examination apparatus is adapted as one of a three-dimensional computer tomography apparatus and a three-dimensional rotational X-ray apparatus.

According to another exemplary embodiment of the present invention, a method of examination of an object of interest with an examination apparatus is provided, the method comprising the steps of providing electrical power and cooling from a stand to an x-ray source of a C-arm module via a connection device, and rotating of the C-arm by more than 360 degrees while providing the electrical power and the cooling.

This may provide for an improved image quality and fast image acquisition, since the C-arm does not have to be moved back after a less than 360 degree rotation.

According to another exemplary embodiment of the present invention, a computer-readable medium is provided, in which a computer program for examination of an object of interest is stored which, when being executed by a processor, causes the processor to carry out the above-mentioned method steps.

Furthermore, according to another exemplary embodiment of the present invention, a program element for examination of an object of interest is provided, which, when being executed by a processor, causes the processor to carry out the above-mentioned method steps.

The method of examination of the object of interest may be embodied as the computer program, i.e. by software, or may be embodied using one or more special electronic optimization circuits, i.e. in hardware, or the method may be embodied in hybrid form, i.e., by means of software components and hardware components.

The program element according to an exemplary embodiment of the invention is preferably loaded into working memories of a data processor. The data processor may thus be equipped to carry out embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that an examination apparatus is provided which has a connection device which is capable of storing a plurality of rotations without taking damage or which has a clutch like element capable of absorbing rotations of the C-arm without disconnecting the high voltage energy supply and the coolant supply from the stand to the C-arm module.

These and other aspects of the present invention will become apparent from and elucidated with reference to the embodiments described hereinafter.

Exemplary embodiments of the present invention will be described in the following, with reference to the following drawings.

The illustration in the drawings is schematic. In different drawings, similar or identical elements are provided with the same reference numerals.

Figure 1:
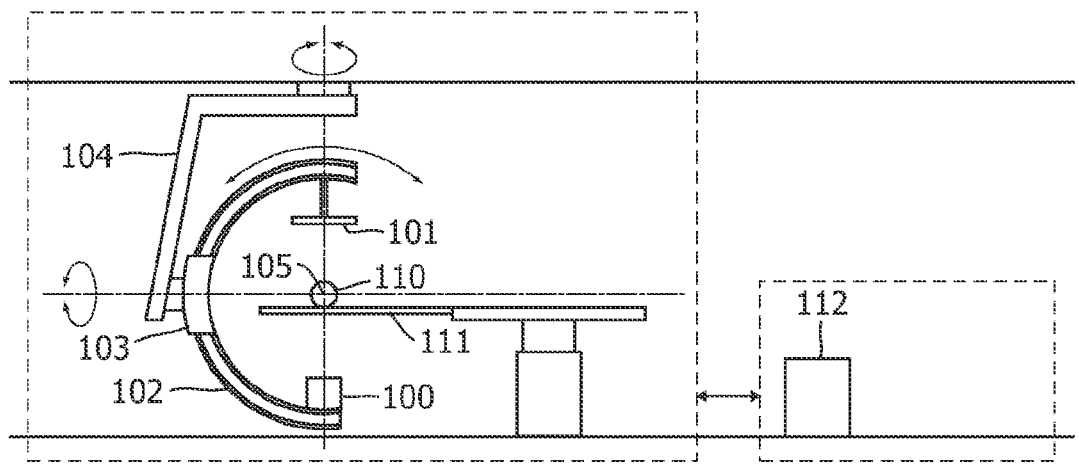
FIG. 1 shows a simplified schematic representation of an examination apparatus according to an exemplary embodiment of the present invention.

FIG. 1 shows a schematic representation of an exemplary rotational X-ray scanner according to an exemplary embodiment of the present invention. An X-ray source 100 and a flat detector 101 with a large sensitive area are mounted to the ends of a C-arm 102. The C-arm 102 is held by a curved rail, the "sleeve" 103. The C-arm can slide in the sleeve 103, thereby performing a "roll movement" about the axis of the C-arm. The sleeve 103 is attached to an L-arm 104 via a rotational joint and can perform a "propeller movement" about the axis of this joint. The L-arm 104 is attached to the ceiling via another rotational joint and can perform a rotation about the axis of this joint. The various rotational movements are affected by servomotors. The axes of the three rotational movements and the cone-beam axis always meet in a single fixed point, the "isocentre" 105 of the rotational X-ray scanner. There is a certain volume around the isocentre that is projected by all cone-beams along the source trajectory. The shape and size of this volume of projection depend on the shape and size of the detector and on the source trajectory. In FIG. 1, the ball 110 indicates the biggest isocentric ball that fits into the volume of projection. The object (for example a patient or an item of baggage) to be imaged is placed on the table 111 such that the object's volume of interest fills the volume of projection. If the object is small enough, it will fit completely into the volume of projection; otherwise, not. The volume of projection therefore limits the size of the volume of interest.

The various rotational movements are controlled by a control unit 112. Each triple of C-arm angle, sleeve angle, and L-arm angle defines a position of the X-ray source. By varying these angles with time, the source can be made to move along a prescribed source trajectory. The detector at the other end of the C-arm makes a corresponding movement. The source trajectory will be confined to the surface of an isocentric sphere.

Figure 2:
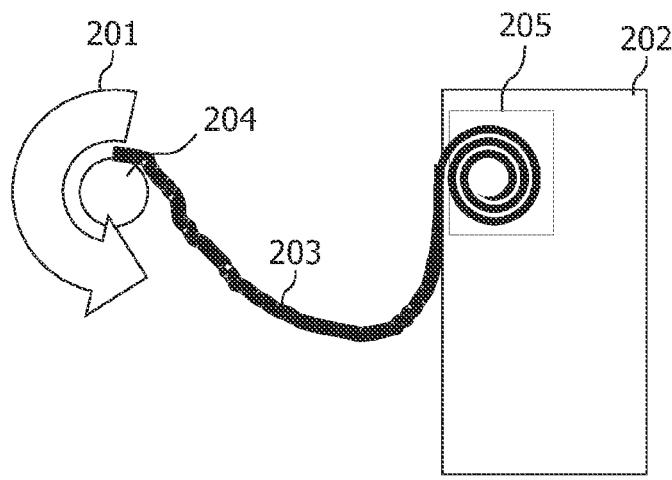
FIG. 2 shows a simplified schematic representation of a layout of an examination apparatus according to an exemplary embodiment of the present invention.

FIG. 2 shows a C-arm system that has a long cable/hose 203 connecting the stand 202 (i.e. the power cabinet and cooling device) to the C-arm 201 according to an exemplary embodiment of the present invention. Furthermore, a storing device 205 is provided, for example within the power cabinet and cooling device 202. Therefore, part of the cable 203 is stored for example at an extreme of the rotational angle.

In other words, before storing the cable 203 partly inside the storing device 205, the C-arm 204 is rotated in one direction until the extreme of the rotational angle is reached. Then, the part of the cable to be stored is wound up inside the storing device 205. Then, during data acquisition, when the C-arm 204 is rotated in the other direction, the stored cable parts are released from the storing device 205, thereby enabling a plurality of rotations of the C-arm.

In other words, the storing device 205 feeds more length of hose to the C-arm as the C-arm 201 rotates around the rotational axis 204. For example, this may provide for four to 10 rotations without reaching the end of the hose 203.

The cable/hose 203 may comprise a high-voltage cable for supplying the x-ray source with electrical energy, a cooling hose for cooling the x-ray source, an earthing wire, geo wiring and detector wiring.

The cable length may, for example, be 26 metres overall, the diameter of the hose may be 8 cm and the radius of rotation may be 30 or 50 cm.

Figure 3:
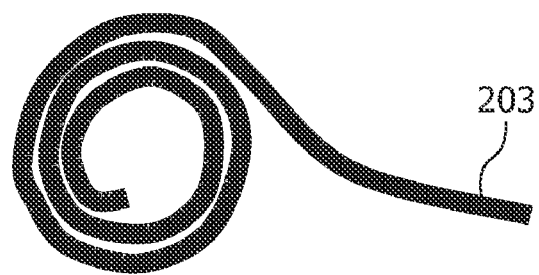
FIG. 3 shows an exemplary embodiment of a connection device (cable/hose) partly wound up for storage.

FIG. 3 shows an exemplary embodiment of a storing device comprising a cable/hose 203 being partly wound up for cable storage. 2.5 rotations may suffice for enabling a plurality of rotations of the C-arm.

Figure 4A:
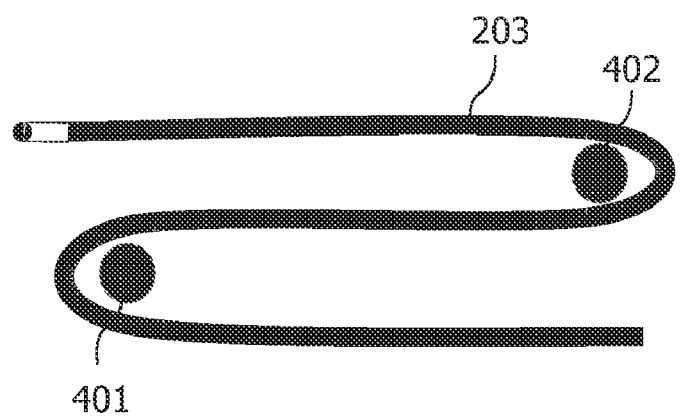
FIG. 4a shows another cable/hose storage in a wound up state according to another exemplary embodiment of the present invention.

FIG. 4a shows a cable storing device according to another exemplary embodiment of the present invention. Here, the cable/hose 203 is wound up around two round elements 401, 402.

Figure 4B:
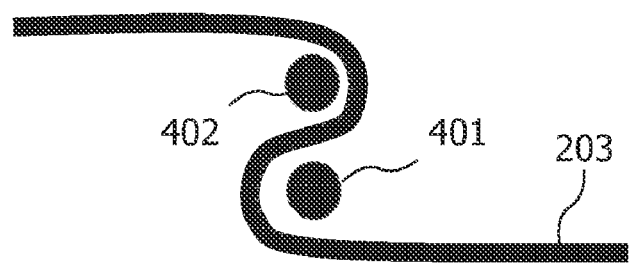
FIG. 4b shows the cable storage of FIG. 4a in an extended state.

FIG. 4b shows the cable storing device of FIG. 4a in an extended state, in which the two round elements 401, 402 are moved together in order to release a part of the cable 203 for enabling a further rotation of the C-arm.

It should be noted, however, that other storage devices are possible.

Figure 5:
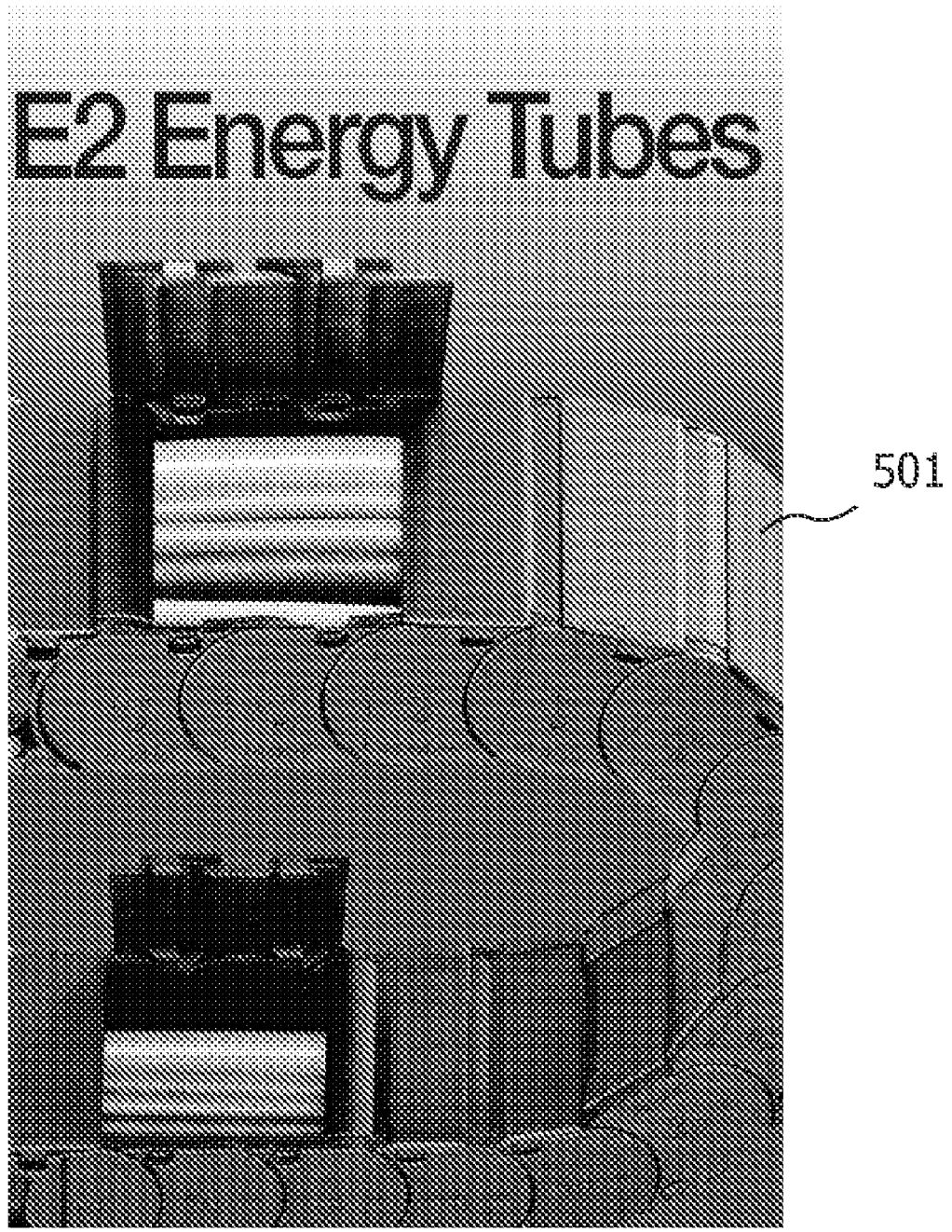
FIG. 5 shows a square cable feeder for cable storage according to another exemplary embodiment of the present invention.

FIG. 5 shows a hose and supply cable being integrated in a square cable feeder/hose 501 that can only bend or roll in one direction. Such a square cable feeder/hose or energy chain is adapted for rolling up the cable and for cable protection, making sure that no mechanical damage to the cable occurs while being wound up and stored inside the storing device 205.

Figure 6:
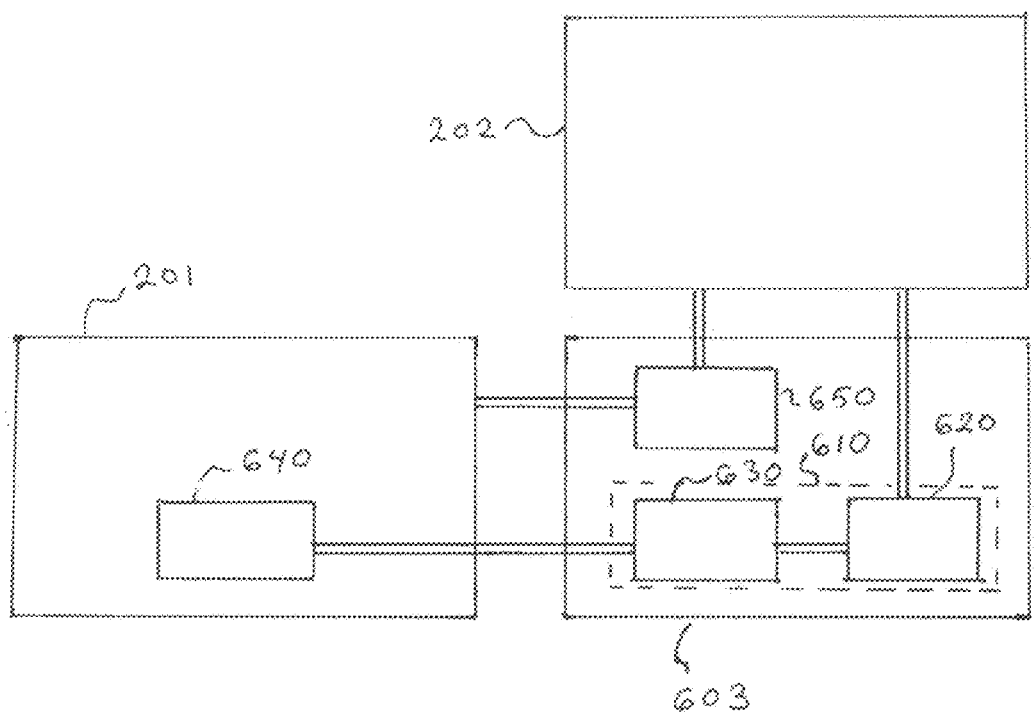
FIG. 6 shows a connection device connected to a C-arm module and to a stand according to the present invention.

According to another exemplary embodiment of the present invention as shown in FIG. 6 in which the C-arm 201 is connected to the C-arm stand 202 via the connection device 603, the C-arm stand is provided with a slip-ring 610. A double solid line between two structures in FIG. 6 denotes connection between the structures. The slip-ring 610 may allow the electrical signal to pass from the stand 202 to the C-arm 201 via sliding fingers 620 that are resting on the ring 630 which in turn are connected to the electrical parts 640 of the C-arm. Also, the cooling fluid may be passed via a rotating coupling 650. The slip-ring 610 is adapted for high-voltage in the range of 140 kV.

The present invention may in particular be implemented in a C-arm system adapted for performing XperCT for which currently only scans of 180 degrees plus fan-beam angle (about 200 degrees) can be made. This may provide for a significantly improved image quality.

Furthermore, the invention may be implemented for three-dimensional rotational angiography (3DRA), thereby increasing the maximum rotational speed.

By expanding the scan range, a system with "limited" motor power may take up more angular range to accelerate, achieving a much higher maximum rotational speed, for example 100 degrees per second or more. Therefore, a 3DRA run may be made in two seconds at 60 frames per second, thereby saving 50% contrast agent dose.

Furthermore, the invention may be implemented in cardiac four-dimensional (three dimensions plus time) x-ray imaging, in which having multiple rotations available may allow to more finely sample the two-dimensional projections over the phases of the electrocardiogram of the patient. The speed of the C-arm may be adapted to match the heart rate of the patient to get optimal sampling over the electrocardiogram.

Furthermore, aspects of the invention may be implemented for perfusion imaging of the brain. Here, having functional information on the brain (perfusion data) is key to evaluate the outcome of a neurological intervention. Currently, this may only be achieved on the CT scanners and MR scanners, whereas the intervention is done on a C-arm system.

Figure 7:
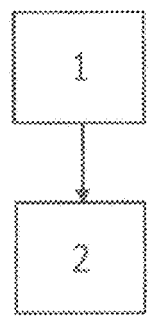
FIG. 7 shows a flow-chart plan exemplary method according to the present invention.

FIG. 7 shows a flow-chart of an exemplary method according to the present invention for examination of an object of interest. The method starts at step 1 with the provision of electrical power and cooling from a stand to an x-ray source of a C-arm module via a connection device. Then, at step 2, the C-arm is rotated by more than 360 degrees during data acquisition while providing the electrical power and the cooling in a continuous mode.

Figure 8:
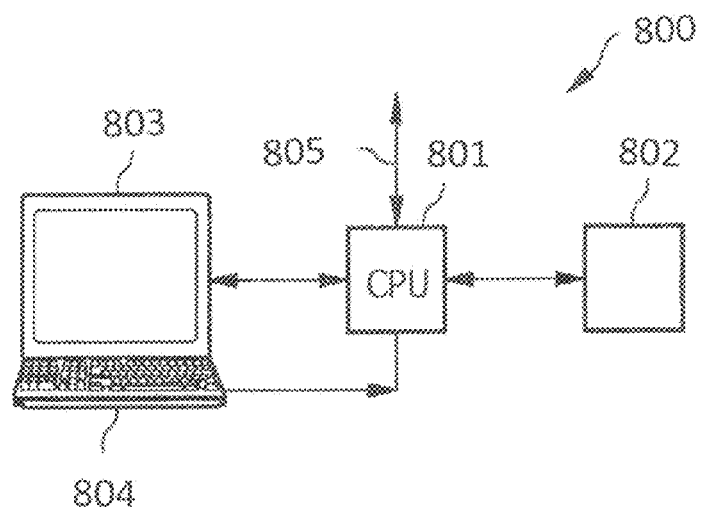
FIG. 8 shows an exemplary embodiment of a processing device according to the present invention for executing an exemplary embodiment of a method in accordance with the present invention.

FIG. 8 shows an exemplary embodiment of a data processing device 800 according to the present invention for executing an exemplary embodiment of a method in accordance with the present invention.

The data processing device 800 depicted in FIG. 8 comprises a central processing unit (CPU) or image processor 801 connected to a memory 802 for storing an image depicting an object of interest, such as a patient or an item of baggage. The data processor 801 may be connected to a plurality of input/output network or diagnosis devices, such as a X-ray C-arm apparatus. The data processor 801 may furthermore be connected to a display device 803, for example, a computer monitor, for displaying information or an image computed or adapted in the data processor. An operator or user may interact with the data processor 801 via a keyboard 804 and/or other input or output devices, which are not depicted in FIG. 8.

Furthermore, via the bus system 805, it may also be possible to connect the image processing and control processor 801 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

Exemplary embodiments of the invention may be sold as a software option to CT scanner console, imaging workstations or PACS workstations.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. Examination apparatus for examination of an object of interest, the examination apparatus comprising: an x-ray C-arm module comprising a C-arm and an x-ray source; a stand for providing electrical power and cooling to the x-ray source; a connection device for providing a connection between the stand and the C-arm module for delivering the electrical power and the cooling to the x-ray source; wherein the connection device is configured for enabling a rotation of the C-arm of more than 360 degrees.

2. The examination apparatus of claim 1, wherein the connection device comprises: a slip-ring for passing electrical signals and the electrical power from the stand to the C-arm module.

3. The examination apparatus of claim 2, wherein the slip-ring comprises a ring and sliding fingers; wherein the sliding fingers are configured for sliding on the ring during rotation of the C-arm, thereby enabling the rotation and meanwhile maintaining electrical contact between corresponding electrical elements of the stand and electrical elements of the C-arm.

4. The examination apparatus of claim 1, wherein the connection device comprises: a rotating coupling for passing coolant from the stand to the C-arm module during rotation of the C-arm.

5. The examination apparatus of claim 1, wherein the connection device comprises: a cable for delivering the electrical power to the x-ray source and being arranged inside a hose; wherein the arrangement of cable and hose is configured for storing at least four rotations of the C-arm.

6. The examination apparatus of claim 5, further comprising: a storing device for storing a part of the cable and adapted for gradually releasing the stored cable during the rotation of the C-arm.

7. The examination apparatus of claim 6, wherein the storing device is configured as a square cable feeder that can only bend or roll in one direction.

8. The examination apparatus of claim 1, wherein the x-ray source is adapted for generating a polychromatic x-ray beam.

9. The examination apparatus of claim 1, being adapted as one of a three-dimensional computed tomography apparatus and a three-dimensional rotational X-ray apparatus.

10. The examination apparatus of claim 1, configured as one of the group consisting of a material testing apparatus and a medical application apparatus.

11. The examination apparatus of claim 1, said rotation being beyond a complete rotation of said C-arm, so that said more than 360 degrees are traversed.

12. A method of examination of an object of interest with an examination apparatus, method comprising the steps of: providing electrical power and cooling from a stand to an x-ray source of a C-arm module via a connection device; rotating of the C-arm by more than 360 degrees while providing the electrical power and the cooling.

13. The method of claim 12, said rotating being beyond a complete rotation of said C-arm, so that said more than 360 degrees are traversed.

14. A non-transitory, computer-readable medium, in which a computer program for examination of an object of interest is stored which, when executed by a processor, causes the processor to carry out the steps of: providing electrical power and cooling from a stand to an x-ray source of a C-arm module via a connection device; rotating of the C-arm by more than 360 degrees while providing the electrical power and the cooling.

15. The computer-readable medium of claim 14, said connection device being configured for enabling said rotating by at least 1440 degrees thereby resulting in at least 4 complete rotations of said C-arm.

16. The computer-readable medium of claim 14, said rotating being beyond a complete rotation of said C-arm, so that said more than 360 degrees are traversed.

17. A method for making an apparatus for examination of an object of interest, the apparatus comprising: an x-ray C-arm module comprising a C-arm and an x-ray source; a stand for providing electrical power and cooling to the x-ray source; and a connection device for providing a connection between the stand and the C-arm module for delivering the electrical power and the cooling to the x-ray source, said method comprising:

configuring the connection device for enabling, while said electrical power and said cooling are being delivered to said x-ray source, a rotation of the C-arm of more than 360 degrees.

18. The method of claim 17, wherein said configuring enables, while said electrical power and said cooling are being delivered to said x-ray source, rotation of said C-arm by at least 1440 degrees thereby resulting in at least 4 complete rotations of said C-arm.

19. The method of claim 17, said rotation being beyond a complete rotation of said C-arm, so that said more than 360 degrees are traversed.

* * * * *